United States Patent [19]

Glossman

[11] Patent Number: 4,784,958

[45] Date of Patent: Nov. 15, 1988

[54] 1,4-DIHYDROPYRIDINE DERIVATIVES AND 1,4-DIHYDROQUINOLINE DERIVATIVES RADIOACTIVELY LABELLED WITH 125I, THEIR PREPARATION, AND THEIR USE IN TESTING MEDICAMENTS

[76] Inventor: Hartmut Glossman, Margenteuweg 4, D-6301 Neuchelheim, Fed. Rep. of Germany

[21] Appl. No.: 672,681

[22] Filed: Nov. 19, 1984

[30] Foreign Application Priority Data

Nov. 19, 1983 [DE] Fed. Rep. of Germany ....... 3341806

[51] Int. Cl.[4] .................. C07D 213/55; C07D 215/16; C07D 403/12; G01N 33/534
[52] U.S. Cl. .................................... 436/504; 436/804; 546/174; 546/278; 546/283; 546/284; 546/321
[58] Field of Search ............... 546/278, 283, 284, 321, 546/174; 436/501, 804, 504; 424/1.1

[56] References Cited

FOREIGN PATENT DOCUMENTS 2739922 3/1979 Fed. Rep. of Germany .

OTHER PUBLICATIONS

*Journal Lab. Clin. Med.*, 89, pp. 902 to 909 (1977), (*Chem. Abs.* 86, 185436P (1977).
J. E. T. Corrie et al., *Meth. Enzymol*, 73 Part B, 79–112, 1981.
R. Quirion, *Neurosci. Lett.*, 36, 267–271, 1983.
FEMS, Microbiological Letter 10, pp. 107–109 (1981), (Chem. Abstracts 94, 170508e (1981).
Journal Immunoassay 4, pp. 83–98 (1983) (Chem. Abstracts 98, 172409e (1983).
Chemical Abstracts, vol. 84, No. 15, Jun. 24th, 1976, p. 17, reference No. 173596m.

*Primary Examiner*—Sidney Marantz
*Assistant Examiner*—David A. Saunders
*Attorney, Agent, or Firm*—Keil & Weinkauf

[57] ABSTRACT

A simple method for preparing highly radioactive 1,4-dihydropyridine and 1,4-dihydroquinoline derivatives labelled with $^{125}$I enables a specific radioactivity of approx. 2200 to 8800 Ci/m Mole to be achieved. In this way high sensitivity in medicament screening with the aid of radioreceptor assays and in determining plasma levels of 1,4-dihydropyridines, 1,4-dihydroquinolines and other substances that inter-react with receptors for 1,4-dihydropyridines and 1,4-dihydroquinolines is achieved, with the result that a substantially shorter exposure time in the auto-radiographic identification of the receptors for these substances is required. For this purpose an amino derivative of a 1,4-dihydropyridine or 1,4-dihydroquinoline is reacted with an acylating reagent radiactively labelled with [125]I (2200–4400 Ci/m-Mole), and the $^{125}$I-substituted 1,4-dihydropyridine or 1,4-dihydroquinoline derivative possessing the specific radioactivity of the acylating reagent is isolated by conventional known separation methods.

10 Claims, 2 Drawing Sheets

1,4-DIHYDROPYRIDINE DERIVATIVES AND 1,4-DIHYDROQUINOLINE DERIVATIVES RADIOACTIVELY LABELLED WITH $^{125}$I, THEIR PREPARATION, AND THEIR USE IN TESTING MEDICAMENTS

BACKGROUND OF THE INVENTION AND PRIOR ART

The invention relates to highly radioactive 1,4-dihydropyridine derivatives and 1,4-dihydroquinoline derivatives labelled with $^{125}$I, their preparation by reacting 1,4-dihydropyridine esters or 1,4-dihydroquinoline esters bearing a terminal amino group on the ester group with $^{125}$I-labelled acylating compounds, and the use of the compounds separated by preparative chromatographic methods for testing medicaments or other substances with the aid of receptors (medicament screening with the aid of radio-receptor assays) and for measuring the plasma levels of calcium channel active medicaments.

A rapid, autoradiographic identification of receptor binding sites of medicaments and other substances that interact with 1,4-dihydropyridine or 1,4-dihydroquinoline binding sites (receptors), is thereby also possible.

The term "organic calcium antagonists" (A. Fleckenstein: Calcium Antagonism in Heart and Smooth Muscle, John Wiley and Sons, New York, Clinchester, Bristone, Singapore, 1983; D. J. Triggle: Calcium Antagonists: Basic Chemical and Pharmacological Aspects (p.p. 1-18) in G. B. Weiss (Editor): New Perspective on Calcium Antagonists, American Physiological Society, Bethseda, Md., USA., 1981; D. J. Triggle: Chemical Pharmacology of Calcium Antagonists (p.p. 17-38) in R. G. Rahwan and D. T. Witiak (eds.): Calcium Regulation by Calcium Antagonists. ACS Symposium Series 201. American Chemical Society, Washington, DC, 1982) covers substances used as therapeutics in man and which have the following areas of application at the present time: angina pectoris, supraventricular tachycardia, ventricular cardiac rhythm disturbances, artrial flutter and atrial fibrillation, raised blood pressure, and are mentioned as suitable for the following possible areas of application: cerebral insufficiency and vasospasm, high pulmonary pressure, bronchial asthma, premature birth, dysmenorrhoea, cardiac protection, arteriosclerosis and blocking of the release of so-called mediators (Thromboxan A$_2$) in allergic or inflammatory disorders or disorders involving blood platelet aggregation (A. Fleckenstein in: Calcium Antagonism in Heart and Smooth Muscle, 1983 and R. A. Janis and D. J. Triggle in: New Developments in Ca$^{2+}$ Channel Antagonists. J. Med. Chem. 26, 775-785, 1983).

The therapeutically used calcium antagonists and calcium antagonists in the clinical trial or development stage belong to various chemical classes. 1,4-dihydropyridines and 1,4-dihydroquinolines are far and away the most effective of the hitherto known calcium antagonists.

Even in concentrations of $10^{-10}$–$10^{-9}$ mole/liter these substances block the passage of calcium through the calcium channels of smooth muscle cell membranes (A. Fleckenstein, 1983; D. J. Triggle, 1981, 1982; R. A. Janis and D. J. Triggle, 1983). This blocking is stereoselective in the case of chiral 1,4-dihydropyridines (Towart, R., Wehinger, E. and Meyer, H. (1981): Effects of unsymmetrical ester substituted 1,4-dihydropyridine derivatives and their optical isomers on contraction of smooth muscle. Naunyn-Schmiedeberg's Arch. Pharmacol. 317: 183-185; Towart R., Wehinger, E., Meyer, H., Kazda, S. (1982): The effects of nimodipine, its optical isomers and metabolites on isolated vascular smooth muscle. Arzneim. Forsch. Drug Res) The following publications: Glossmann, H., Ferry, D. R., Lübbecke, F., Mewes, R., Hoffman, F. (1982): Calcium channels: direct identification with radioligand binding studies. TIPS 3: 431-437; Glossman, H. and Ferry, D. R. (1983): Molecular approach to the calcium channel. Drug Development 9: 63-98; Janis, R. A., Triggle, D. J. (1983): New developments in Ca$^{2+}$ channel antagonists. J. Med. Chem. 26; 775-785; Janis, R. A., Scriabine, A. (1983): Sites of action of Ca$^{2+}$ channel inhibitors. Biochem. Pharmacol. (in press); Ferry, D. R., Goll, A., Glossmann, H. (1983): Differential labelling of putative skeletal muscle calcium channels by $^3$H-nifedipine, $^3$H-nitrendipine, $^3$H-nimodipine and $^3$H-PN200-110. Nauyn-Schmiedeberg's Arch. Pharmacol. 323: 276-277; Bellemann, P., Ferry, D. R., Lübbecke, F., Glossmann, H. (1981); $^3$H-nitrendipine, a potent calcium antagonist binds with high affinity to cardiac membranes. Arzneim-Forsch (Drug Res) 31: 2064-2067; Ferry, D. R., Glossmann, H. (1982a): Identification of putative calcium channels in skeletal muscle microsomes. FEBS Lett 148: 331-337; Ferry, D. R., Glossmann, H. (1982b): Evidence for multiple drug receptor sites within the putative calcium channel. Naunyn-Schmiedeberg's Arch. Pharmacol. 321: 80-83, describe, inter alia, in review articles the use of Tritiated (specific activity approx. 3-approx. 160 Ci/mMole) 1,4-dihydropyridines to characterise the binding sites (receptors) for these phamraceuticals. Tritiated 1,4-dihydropyridines may be used, on the basis of this knowledge of in vitro screening of new substances, to elucidate specific side effects of known medicaments or to measure the plasma level of calcium antagonists. (Examples: R. J. Gould, K. M. M. Murphy, I. J. Reynolds and S. H. Snyder: Thioridazine: Calcium channel blockade may explain peripheral side effects. American J. Psychiatrics (in press) and R. J. Gould, K. M. M. Murphy and S. H. Snyder: A simple radioreceptor assay for calcium antagonist drugs.

Life Sciences (in press)). Tritiated 1,4-dihydropyridines are also used in the autoradiographic identification of their receptors (e.g. Quirion, R. (1983): Autoradiographic localisation of a calcium channel antagonist. $^3$H-nitrendipine, binding site in rat brain (Neuroscience Lett 36: 267-271).

According to the present state of the art and current regulations concerning the elimination of radioactive waste, tritiated compounds are no longer regarded as optimum substances for the afore-mentioned examples of use. Disadvantages of $^3$H compared with, for example, $^{125}$I are the long half-life value, the relatively low specific activity and therefore reduced sensitivity, the need to use organic scintillators, the poor counting efficiency, and the long exposure times for the purposes of autoradiography.

The problems of high level radioactive labelling with $^{125}$I of substances that act for example as haptens and are used as ligands in a radioimmunoassay have been exhaustively discussed by J. E. Corrie and W. M. Hunter (Methods in Enzymology Vol. 73, Part B, Eds. J. L. Langone and H. van Vunakis, Academic Press. New York, London, Toronto, Sydney, San Francisco, 1981, p.p. 79-112). According to them, it is of paramount importance that the ligand produced is analytically effective in the field of application, that the radioactive labelling is reproducible, and that the ligand exhibits a low non-specific binding and can be stored in a stable condition for a prolonged period (days, weeks, months). There are in principle three ways of synthesizing stable $^{125}$I-labelled ligands:

1. (And the least used) Halogen exchange reactions (e.g. Science 205, p.p. 1138–1140 (1979))

2. Introduction of $^{125}$I in phenol or imidazole derivatives by means of the chloramine T method according to Greenwood, Hunter and Glover, or electrolytically or by means of lactoperoxidase (very commonly used), and 3. The introduction of radioactive $^{125}$I via a carrier molecule. With a few exceptions (e.g. aminoglycoside antibiotics, Clonazepam, Biotin, Bleomycin) this third method namely the introduction of radioactive $^{125}$I via a carrier molecule, e.g. with $^{125}$I-labelled N-succinimidyl 3-(4-hydroxyphenyl)-propionate, di-$^{125}$I-labelled methyl p-hydroxybenzimidate and $^{125}$I-labelled diazotised aniline, is described only for peptides and proteins or e.g. for heparin (J. J. Langone in: Methods in Enzymology Vol. 73, Part B, Eds. J. L. Langone and H. van Vunakis, Academic Press, New York, London, Toronto, Sydney, San Francisco, 1981, p.p. 112–127).

The basic limitation of the method follows from the absolute priority as regards the properties, demanded by J. E. Corrie and W. M. Hunter (ibid.), namely the ligand produced must not only be radioactive, but must also be analytically utilisable. It is therefore not sufficient just to introduce radioactive iodine into a molecule via one of the afore-mentioned methods, in particular method 3; the labelled product must also be recognised, e.g. in a radioimmunoassay, by an antibody directed against it, and must be able to be bound with a sufficient binding strength. The smaller the molecule to be radioactively labelled, the more difficult it becomes to satisfy the structural requirements, in particular for specific binding sites (receptors) of the medicaments, if by means of method 3 a relatively large radioactive substance alters the structure via the introduction of a carrier molecule. These difficulties explain why highly radioactive 1,4-dihydropyridines and 1,4-dihydroquinolines labelled with $^{125}$I that satisfy the necessary criteria do not yet exist.

OBJECTS AND SUMMARY OF THE INVENTION

The object of the invention is to provide new $^{125}$I-labelled 1,4-dihydropyridine derivatives and 1,4-dihyquinoline derivatives which, on the basis of their structure, bind in a highly selective and effective manner to receptors for pharmaceuticals of this class of substances in various tissues.

This objective is achieved by the radioactively labelled 1,4-dihydropyridine derivatives and 1,4-dihydroquinoline derivatives of the following general formula:

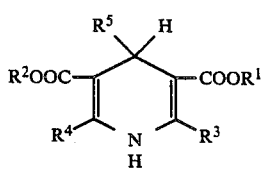

and the 1,4-dihydroquinoline derivatives of the general formula

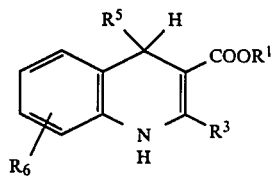

in which R$^2$ and R$^2$ are the same or different and R$^1$ is a

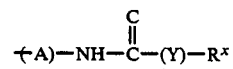

group, in which A and Y are a straight chain or branched alkyl group with 1–6 carbon atoms and R$^x$ is a phenyl radical substituted in the p-position, but not with halogen, or an imidazole radical attached to the 4-position, and if R$^1$ is not the same as R$^2$ then R$^2$ denotes NO$_2$, nitrile or alkoxy with 1–4 carbon atoms, R$^3$ and R$^4$ are the same or different and denote H, NH$_2$ or straight chain or branched alkyl radicals with 1–4 carbon atoms, R$^5$ denotes an aryl radical which optionally contains 1 to 2 identical or different substituents from the group consisting of alkyl, alkoxy, phenyl, halogen, nitro, cyano, trifluoromethyl or alkylmercapto, and is preferably a phenyl, naphthyl, thenyl or furyl radical, R$^6$ denotes H, halogen, an alkyl or alkoxy radical, and in which the radical R$^x$ is also singly or doubly substituted by $^{125}$I and has a specific activity of about 2200 to about 8800 Ci/mMole.

Preferred embodiments of the invention, in particular the preparation and use of the derivatives, are described in the subclaims.

Radioactive labelling with $^{125}$I is effected by introducing a phenyl radical or imidazole radical singly or doubly substituted by radioactive iodine, in specific positions of the 1,4-dihydropyridine or 1,4-dihydroquinoline derivatives. The radioactively labelled radical R$^x$ is preferably a radical of the formulae:

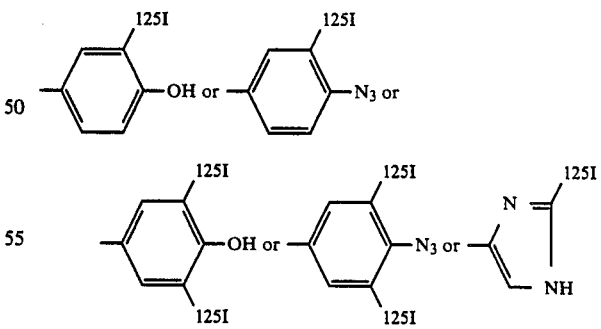

The activities that can thereby be obtained are between about 2200 and about 8800 Ci/mMole, depending on whether the radical R$^x$ is singly or doubly substituted by $^{125}$I, and whether one or two labelled radicals R$^x$ have been introduced into the pyridine derivatives. An activity of 2200 to 6600 Ci/mMole is preferred. Derivatives having activities of about 2200 to about 4400 Ci/mMole are especially preferred since they are particularly stable.

The 1,4-dihydropyridine derivatives and 1,4-dihydroquinoline derivatives according to the invention are synthesized from corresponding carboxylic acid ester derivatives bearing a terminal, unsubstituted amino group on the ester group.

The preparation of both the asymmetrical and symmetrical starting compounds is described in DE-OS Nos. 21 17 573, 23 10 746 and 29 35 451.

In this connection, aldehydes of the formula $R^5CHO$ in which $R^5$ is an aryl radical optionally containing 1 to 2 identical or different substituents from the group comprising alkyl, alkoxy, phenyl, halogen, nitro, cyano, trifluoromethyl or alkylmercapto, wherein alkyl or alkoxy or alkylmercapto are lower groups of this type with 1–4 carbon atoms, are reacted with B-ketocarboxylic acid esters of the formula $R^4CO$—$CH_2$—$COO\,R^2$ and enamine carboxylic acid esters of the formula

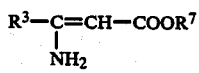

in the presence of water or inert organic solvents at temperatures between 30° and 200° C.

$R^7$ is in these cases a straight chain or branched alkyl group with 1–6 carbon atoms, preferably methyl or ethyl, which, in contrast to the compounds described in the publications, bears a terminal primary amino group.

$R^2$ may be the same as $R^1$ or may be $NO_2$, nitrile or alkoxy with 1–4 carbon atoms.

$R^3$ and $R^4$ are the same or different and denote H, $NH_2$ or straight chain or branched alkyl radicals with 1–4 carbon atoms.

The 1,4-dihydroquinoline derivatives are prepared starting from 2-aminobenzyl alcohols of the formula

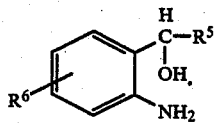

which are reacted with β-dicarbonyl compounds of the formula

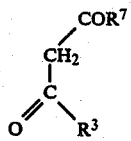

in the presence of inert organic solvents at temperatures between 20° and 200° C. $R^3$, $R^5$ and $R^7$ have the aforementioned meanings. $R^6$ is H, halogen, alkyl or alkoxy with in each case 1–4 carbon atoms, preferably methyl, ethyl, methyloxy or ethyloxy.

$^{125}I$-labelled succinimide esters of the formula

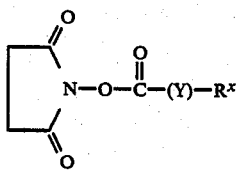

in which Y is a straight chain or branched alkyl group with 1–6 carbon atoms, preferably with 1, 2 or 3 C atoms and $R^x$ is defined hereinbefore, and wherein this radical is singly or doubly substituted with $^{125}I$, serve as acylating compounds for introducing the radioactively labelled radical $R_x$.

The reaction is carried out as described by J. J. Langone in Methods in Enzymology, Vol. 70, p.p. 221–243 (1980) under mild conditions between 0° and 25° C. within 5 or more minutes in a suitable solvent, preferably in the alkaline range e.g. with the addition of sodium borate buffer, pH 8.4–8.5.

The reaction products are preparatively separated by chromatographic methods (HPLC or thin layer chromatography), and the dihydropyridine and dihydroquinoline derivatives according to the invention are taken up in benzene or absolute ethanol and stored at −20° C. in the absence of light and oxygen. The derivatives have the specific activity of the employed succinimide ester. This activity is preferably between 2200 and 4400 Ci/mMole.

The radiochemical purity is checked by conventional chromatographic methods (HPLC or thin layer chromatography). The necessary stability under the conditions of use of the compounds according to the invention for testing medicaments may also be checked by the same method.

In this connection the $^{125}I$-labelled 1,4-dihydropyridine and 1,4-dihydroquinoline derivatives are combined in the socalled receptor assay (buffers, elevated temperature between 25° and 37° C.) with tissue homogenates, plasma and membrane fractions. The specific binding is measured, this being defined as the difference between the binding of the labelled derivative in the absence and presence of 1 μmole/l of a pharmaceutical of comparable structure or one having a similar effect. Bound and free $^{125}I$-labelled derivatives are separated by conventional filtration techniques, as are described for example by J. P. Bennett: Methods in binding studies, in: Neurotransmitter Receptor Binding (Eds. H. J. Yamamura, S. J. Enna and M. J. Kuhar, Raven Press, N.Y. 1978 p.p. 57–90).

To separate the free ligand from the bound ligand, 10% (w/v) polyethylene glycol 6000 was added to ice-cold 10 mM TRIS HCl buffer, pH 7.4, 20 mM $MgCl_2$ (3.5 ml), the sample was diluted, suction filtered in vacuo through a glass fibre filter, and the glass fibre filter was washed twice with 3.5 ml of the same buffer. The particle-bound radioactivity retained on the filter was then measured.

The labelled derivatives according to the invention are a particularly advantageous means of testing medicaments by in vitro tests and are suitable for the autoradiographic identification of medicament receptor binding sites and blood plasma level determination of calcium channel-active medicaments such as Ca antagonists. The advantages achieved by the invention are as follows:

$^{125}I$-labelled ligands are preferred to tritiated compounds for areas of application as described by us, since:

1. The specific radioactivity of $^{125}I$ is substantially higher (up to 100 times higher) than that of tritium, 2. The radioactivity can be measured more cheaply (no scintillators), 3. No organic solvent waste has to be eliminated, in contrast to the case with tritium, 4. A higher sensitivity in the radioreceptor assay is achieved, 5. The elimination of the radioactive waste does not present any problems on account of the shorter half-lifetime of $^{125}I$ (60 days as compared with 12 years), 6. Shorter exposure times (only 1–2 days instead of 30–90 days) are required for the autoradiographic identification, 7. The preparation of the labelled ligands is possible on a technical scale and is also simple and reproducible, and 8. The costs of the preparation are far below those of the tritiated compounds.

If asymmetrical 1,4-dihydropyridine derivatives are prepared by synthesizing compounds in which the radicals $R^1$ and $R^2$ are not the same, a racemate is formed. The diastereomers formed on account of the two possible configurations at the $C_4$-atom of the dihydropyridine ring may be separated by conventional known methods. Depending on whether both or only one of the configurations are to be radioactively labelled, the separation may be performed before or after the reaction with the succinimide ester. A prior separation of the mixture is particularly preferred however in order to be able to selectively label the desired form in each case. The particular advantage is the fact that the two diastereomers have different binding behaviours to receptors and may therefore be differentiated.

BRIEF DESCRIPTION OF THE DRAWINGS

Further objects and advantages will become apparent upon reading the following examples wherein the invention is described in more detail in conjunction with the drawings wherein.

EXAMPLE 1

Figure 1B:
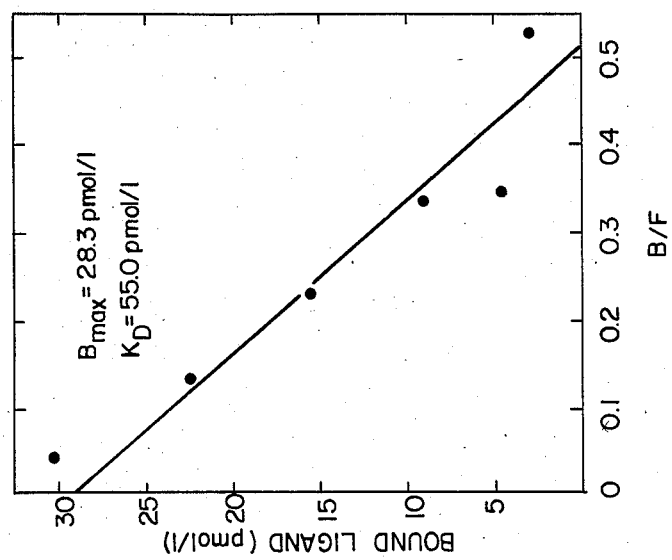
FIG. 1B plots the transformation of the binding data according to G. Scatchard.

1,4-dihydro-2,6-dimethyl-4(2-trifluoromethyl-phenyl)-3,5-dicarboxylate-(2-amino)ethyl ester pyridine is reacted with singly 125I-labelled monoiodosuccinimide ester according to the following reaction scheme:

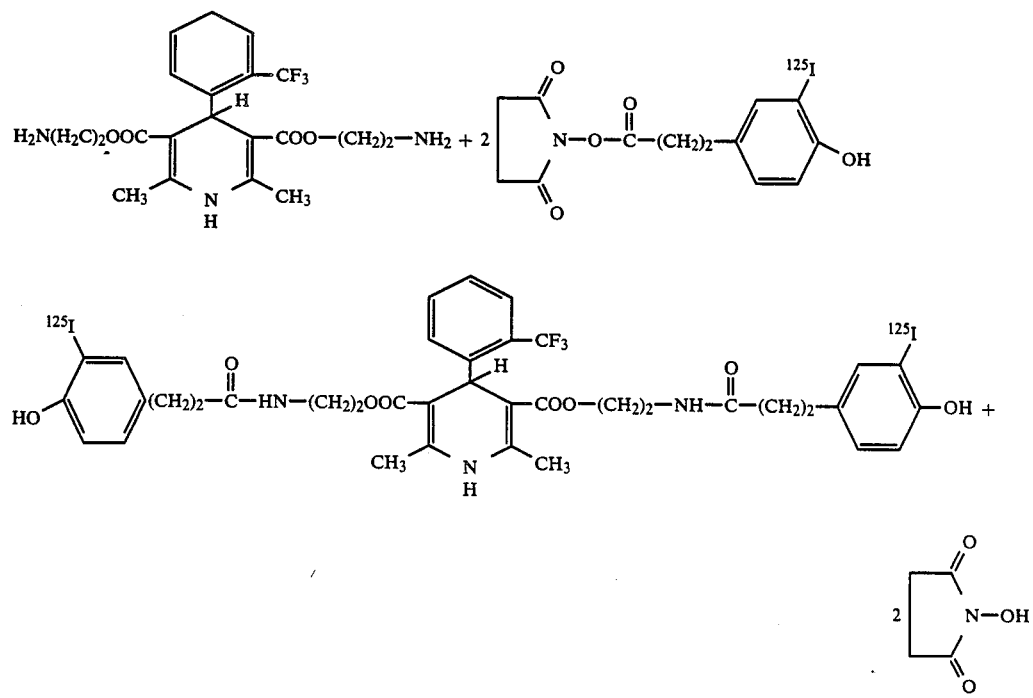

The succinimide ester was prepared according to Bolton and Hunter (Biochem. J. (1973) 133, 529–533) or, alternatively, was obtained from Amersham-Buchler (Braunschweig), with a specific activity of approx. 2200 Ci/mMole.

Preparation of $^{125}$iodo[1,4-dihydro-2,6-dimethyl-4-(2-trifluoromethylphenyl)-3,5-dicarboxylate-(2-(1-(3-iodo-4-hydroxyphenyl)-3-oxo-propyl)amino)-ethyl ester pyridine] (under Na light):

0.90 nmole (~1 mCi) of the succinimide ester (in benzene) is dried under a stream of nitrogen and 2.5 nmole of the 1,4-dihydropyridine aminoethyl ester in 5 μl of absolute ethanol is added thereto. After addition of 5 μl 100 mmole/l sodium borate buffer (pH 8.4) and incubating for 20 minutes on ice, the reaction products are separated preparatively by thin layer chromatography under sodium light. Ethyl acetate/diethyl ether (30:70 v/v) was used as solvent system and silica gel 60 (Merck AG, Darmstadt) was used as carrier. The iodinated 1,4-dihydropyridine derivative runs in this solvent system, whereas the unreacted 1,4-dihydropyridine aminoethyl ester remains at the start. The derivative according to the invention is extracted with absolute ethanol and stored either in benzene or absolute ethanol at −20° C. (in the absence of oxygen and light). Thus, the $^{125}$I-labelled 1,4-dihydropyridine derivative, which is obtained in good yield (40±10%; mean value±standard deviation from 3 batches, of the introduced radioactivity), has the specific activity corresponding to that of the succinimide ester employed (approx. 2200 Ci/mMole), i.e. 4400 Ci/mMole. The radiochemical purity is checked by conventional methods (HPLC, thin layer chromatography).

EXAMPLE 2

1,4-dihydro-2,6-dimethyl-4-(2-trifluoromethylphenyl)-3-carboxylate ethyl ester-5-carboxylate-(2-amino)-ethyl ester pyridine is reacted with singly $^{125}$I-labelled monoiodosuccinimide ester. The succinimide ester is the same as in Example 1 and has a specific activity of approx. 2200 Ci/mMole.

Preparation of $^{125}$Iodo[1,4-dihydro-2,6-dimethyl-4(2-trifluoromethylphenyl)-3-carboxylate ethyl ester-5-carboxylate-(2-(1-3-iodo-4-hydroxyphenyl)-3-oxopropyl-)amino)-ethyl ester pyridine] under Na light: the procedure is substantially the same as in Example 1, though only 1 mole of succinimide ester is used per mole of aminoethyl ester.

0.45 nmole (~1 mCi) of the succinimide ester (in benzene) is dried under a stream of nitrogen and 2.5 nmole of the 1,4-dihydropyridine aminoethyl ester in 5 μl absolute ethanol is added thereto. After adding 5 μl of 100 mmole/l sodium borate buffer (pH 8.4) and incubating for 20 minutes on ice, the reaction products are separated preparatively by means of thin layer chromatography under sodium light. Ethyl acetate/diethyl ether (30:70 v/v) was used as solvent system, and silica gel 6 (Merck AG, Darmstadt) was used as carrier. The iodinated 1,4-dihydropyridine has a $R_F$-value of 0.35 in this solvent system, whereas the unreacted 1,4-dihydropyridine aminoethyl ester remains at the start. The derivative according to the invention is extracted with absolute ethanol and stored either in benzene or absolute ethanol at $-20°$ C. (in the absence of oxygen and light). The $^{125}$I-labelled 1,4-dihydropyridine derivative, which is obtained in good yield (40±10%; mean value±standard deviation from 3 batches, of the introduced radioactivity), has the specific activity corresponding to that of the succinimide ester employed (approx. 2200 Ci/mMole), i.e. 2200 Ci/mMole. The radiochemical purity is checked by means of conventional methods (HPLC, thin layer chromatography).

Use of the derivative prepared as described hereinbefore for testing medicaments:

Aliquots of the obtained and $^{125}$I-labelled 1,4-dihydropyridine are dried in a stream of nitrogen, incubated with buffer (50 mM TRIS-HCl, pH 7.4, to which the protease inhibitor phenylmethylsulphonyl fluoride has been added (0.1 mmole/l)) and membrane fractions from guinea-pig brain, cardiac muscle and skeletal muscle (prepared as described in Drug Development 9: 63–98 (1983); Naunyn-Schmiedeberg's Arch. Pharmacol. 321: 80–83 (1983) and FEBS Lett 148: 331–337 (1982)) at 25° C. in 0.1 ml volume until equilibrium is reached, and the specific binding (defined as the difference in the binding of the $^{125}$I-labelled 1,4-dihydropyridine in the absence and presence of 1 μmole/l of Nimodipin) is measured by means of the filtration technique (to separate bound and free $^{125}$I-labelled 1,4-dihydropyridine). In order to separate the free ligand from the bound ligand, 10% (w/v) polyethylene glycol 6000 was added to ice-cold 10 mM TRIS HCl buffer, pH 7.4, followed by 20 mM MgCl₂ (3.5 ml), the sample was diluted, suction filtered in vacuo over a glass fibre filter, and the glass fibre filter was rewashed twice with 3.5 ml of the same buffer. The particle-bound radioactivity retained on the filters was then measured. FIG. 1a shows by way of example the saturation analysis (concentration range of the free, $^{125}$I-labelled 1,4-dihydropyridine derivative: 17–1276 pmole/l) of the 1,4-dihydropyridine receptors in guinea-pig brain membranes (20 μg membrane protein per experimental batch) carried out with the aid of the $^{125}$I-labelled 1,4-dihydropyridine derivative.

Figure 1A:
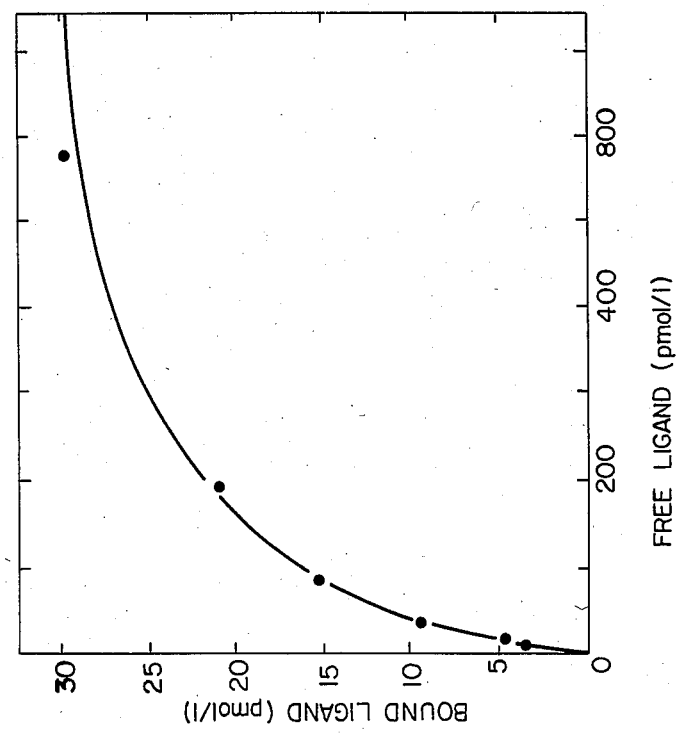
FIG. 1A plots the measured dependence of the concentration of the bound ligand against the concentration of the free ligand.

In FIG. 1A the measured dependence of the concentration of the bound ligand is plotted against the concentration of the free ligand, while in FIG. 1B the transformation of the binding data according to G. Scatchard (Ann. N.Y. Acad. Sci. 51, 660–672, 1949), is plotted, wherein B is the concentration of the bound ligand, F is the free ligand, $K_D$ is the dissociation equilibrium constant, and $B_{Max}$ is the concentration of the highly selective binding sites in the experimental batch. The following formula was used to calculate the concentration of the free ligand: (T. a)-B, where T is the total concentration of the ligand, a is a factor describing the binding capacity of the ligand, and B is the concentration of the specifically bound ligand in equilibrium. The factor a was determined experimentally by saturating the radioactive ligand with binding sites (receptors) (described in FEBS Lett. 148, 331–337, 1982; Naunyn Schmiedeberg's Arch. Pharmacol 321, 7–10, 1982). The factor "a" was 0.5 for the asymmetric 1,4-dihydropyridine derivative, in agreement with the theoretically required capacity of the receptor (R) and (S) to differentiate enantiomers of the $^{125}$I-labelled 1,4-dihydropyridine (stereospecifity of the binding). The $^{125}$I-labelled 1,4-dihydropyridine is the racemic mixture of (R) and (S) enantiomers. A dissociation constant of 350 pmole/l (25° C.) was found for muscle membranes (not illustrated). The stability of the $^{125}$I-labelled 1,4-dihydropyridine was checked under the following conditions by conventional methods (HPLC, thin layeer chromatography): buffer 50 mM TRIS HCl, pH 7.4, 25° C., 4 hours; muscle membrane in buffer, 25° C., 4 hours; as well as storage in benzene or absolute ethanol at $-20°$ C. for up to 21 days after preparation of the ligand. In no case were the radiochemical impurities greater than 10%.

Conclusion:

The $^{125}$I-labelled 1,4-dihydropyridine binds with a dissociation constant of less than 1 nmole/l at 25° C. to guinea-pig brain membranes and skeletal muscle membranes. It exhibits sufficient stability.

EXAMPLE 3

A 1,4-dihydroquinoline derivative was prepared in a similar manner to that described in Example 2.

1,4-dihydro-2-methyl-4-(2-trifluoromethylphenyl)-3-quinoline carboxylate-(2-amino)ethyl ester is reacted with the same succinimide ester as in Example 1.

The reaction products are separated by thin layer chromatography under sodium light. The separated derivative according to the invention is extracted with absolute ethanol and stored for use either in this solvent or in benzene at $-20°$ C. in the absence of light and oxygen. The specific activity of the succinimide ester employed of about 2200 Ci/mMole was transferred. The radiochemical purity was chromatographically checked.

EXAMPLE 4

Table 1 shows results of competition experiments. The data in Table 1 are mean values (±asymptotic standard deviation) from 3 independent experiments in which various calcium antagonists and derivatives or precursors of calcium antagonists were used as competitors with the $^{125}$I-labelled 1,4-dihydropyridine ("ligand") obtained in Example 2. Guinea-pig skeletal muscle membranes were used as receptor material. The concentration of the labelled ligand was 20–30 pmole/l and the experimental temperature was 25° C. 6 to 9 different concentrations of the checked substances were used (in each case as duplicate) and the measured binding data were optimally adapted by means of a computer program (DeLean A., Munson P. J., Rodbard D. (1978). Simultaneous analysis of families of sigmoid curves: application to bioassay, radioligand assay and physiological dose-response curves. Am J. Physiol. 4 E97-102). The stereospecifity of the binding for chiral 1,4-dihydropyridines was investigated as an important criterion for the receptor binding of the $^{125}$I-labelled 1,4-dihydropyridine in group 1. Group 2 contains two 1,4-dihydropyridines that can activate calcium channels, group 3 contains two 1,4-dihydropyridines which are only slightly effective as calcium channel blockers, group 4 contains the enantiomers of Verapamil and Methoxyverapamil, Group 5 contains two diastereomers of Diltiazem, while group 6 contains an inorganic calcium antagonist. The IC$_{50}$ value is the concentration of the substance that produces 50% inhibition of the specific binding of the ligand in the radioreceptor assay. In the case of di-cis-diltiazem the measurements were carried out at 37° C. and the EC$_{50}$ value was determined. The EC$_{50}$ value is the concentration of the substance stimulating a semi-maximum specific binding of the ligand.

Conclusion: $^{125}$I-labelled 1,4-dihydropyridine ("ligand") can be used for the raddioreceptor assay.

TABLE 1

BINDING CONSTANTS FOR UNLABELLED COMPOUNDS DETERMINED WITH THE $^{125}$I-LABELLED 1,4-DIHYDROPYRIDINE PREPARED IN EXAMPLE 2

| GROUP | SUBSTANCE | IC$_{50}$ nmol/l |
|---|---|---|
| 1. | (+)205-033 | 2 ± 0.05 |
|  | (−)205-034 | 198 ± 40 |
|  | (−)Bay e 6927 | 3 ± 0.04 |
|  | (+)Bay e 6927 | 420 ± 67 |
|  | (+)Nicardipine | 7 ± 0.8 |
|  | (−)Nicardipine | 42 ± 3 |
| 2. | Bay K 8644 | 37 ± 5 |
|  | CGP 28392 | 1250 ± 180 |
| 3. | Bay M 5579 | 1860 ± 300 |
|  | Vo 2605 | 320 ± 35 |
| 4. | (−)Methoxyverapamil | 21 ± 8 |
|  | (+)Methoxyverapamil | 190 ± 50 |
|  | (−)Verapamil | 98 ± 22 |
|  | (+)Verapamil | 54 ± 12 |
| 5. | d-cis-Diltiazem | 960 ± 310 |
|  | l-cis-Diltiazem | 3000 ± 1600 |
| 6. | La$^{3+}$ | 110000 ± 20000 |

The individual substances were:

(+) 205–033: (+) enantiomer of PN 200-110 (isopropyl 4-(2,1,3-benzoxadiazole-4-yl)-1,4-dihydro-2,6-dimethyl-5-methoxycarbonylpyridine-3-carboxylate)

(−) 205–034: (−) enantiomer of PN 200-110 (isopropyl 4-(2,1,3-benzoxadiazole-4-yl)-1,4-dihydro-2,6-dimethyl-5-methoxycarbonylpyridine-3-carboxylate)

(+) Bay e 6927: (+) enantiomer of Bay e 6927 (isopropylmethyl 1,4-dihydro-2,6-dimethyl-4-(3-nitrophenyl)-3,5-pyridinedicarboxylate)

(−) Bay e 6927: (−) enantiomer of Bay e 6927 (isopropylmethyl 1,4-dihydro-2,6-dimethyl-4-(3-nitrophenyl)-3,5-pyridinedicarboxylate)

(+) Enantiomer of Nicardipin (2,6-dimethyl-4-(3 nitrophenyl)-1,4-dihydropyridine-3,5-dicarboxylic acid 3-2(N-benzyl-N-methylamino)-ethylester-5-methylester)

(−) Enantiomer of Nicardipin (2,6-dimethyl-4-(3 nitrophenyl)-1,4-dihydropyridine-3,5-dicarboxylic acid 3-2(N-benzyl-N-methylamino)-ethylester 5-methylester)

Bay K 8644: 1,4-dihydro-2,6-dimethyl-4-(2-trifluoromethylphenyl)-3,5-pyridinecarboxylic acid 2-(aminoethyl)ethyl ester CGP 28392: (4-(2-difluoromethoxy)phenyl-1,4,5,7-tetrahydro-2-methyl-5-oxofuro(3,4-b)pyridine-3-carboxylic acid ethyl ester Bay M 5579: Nitrendipin derivative with free carboxyl group (see TIPS 3: 431–437; 1982)

VO 2605: Bromine derivative of PN 200-110 (see Drug Development 9: 63–98; 1982)

EXAMPLE 5

Figure 2:
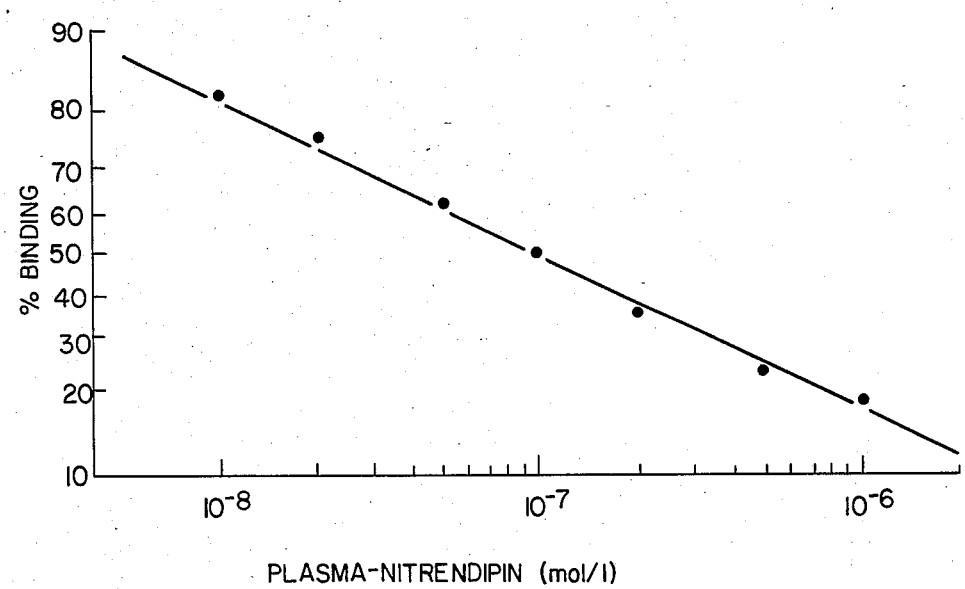
FIG. 2 shows a calibration curve for determining 1,4-dihydropyridine (Nitrendipin) in human plasma.

FIG. 2 shows a calibration curve for determining 1,4-dihydropyridine (Nitrendipin) in human plasma. For this purpose, Nitrendipin was added to EDTA plasma of a fasting experimental subject, and diluted with plasma. Skeletal muscle membranes (guinea-pig) (20 μg protein) and $^{125}$I-labelled 1,4-dihydropyridine derivative (20 pM, prepared as in the description) are added to the various plasma dilutions (10 μl) in an experimental batch of 0.25 ml and the specific binding is measured, after adjusting the equilibrium (2 hours), by means of the customary filtration method described in Example 2. The specific binding data (points) were plotted against the Nitrendipin concentration present in the original plasma, using the conventional method of logit-log transformation (D. Rodbard and G. R. Frazier in: Methods in Enzymology, Vol. 37, Part B, eds. O'-Malley and J. G. Hardman, Academic Press, New York, San Francisco, London, p.p. 1–22, 1975). The standard curve obtained (unbroken line) is a straight line for the Nitrendipin concentrations that produce a 15% and 85% inhibition of the specific binding of the $^{125}$I-labelled ligand compared with the empty phase (=plasma without Nitrendipin).

Conclusion:

The $^{125}$I-labelled 1,4-dihydropyridine derivative enables calcium antagonists to be measured in the blood plasma by means of the radioreceptor assay. The sensitivity is sufficient since the conventional therapeutic concentrations, e.g. for the 1,4-dihydropyridine derivative Nifedipin, are between 70 and 200 nMole/l of plasma.

The Examples illustrate the preparation and use of the 1,4-dihydropyridine derivatives according to the invention as a test reagent for checking medicaments. A similar effect was found for the 1,4-dihydroquinoline derivatives according to the invention. Since it is possible to have a different number of $^{125}$I-substituents on the radical R$^x$, namely one or two substituents, and at the same time it is also possible in the case of the symmetrical dihydropyridine derivatives to react one or two molecules of succinimide ester with one molecule of dihydropyridine carboxylic ester derivative, the method according to the invention provides in each case a sufficient labelling that can be adapted to the structure-specific requirements for synthesizing stable compounds.

The receptors are able to bind only specific molecular structures. The large choice of possible substituents on the 1,4-dihydropyridine and 1,4-dihydroquinoline parent substance enables $^{125}$I-labelled compounds suitable for binding purposes to be prepared for all the usual known receptors of this class of substance.

What is claimed is:

1. A radioactively labelled 1,4-dihydropyridine derivative of the formula

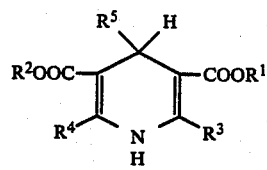

I in which $R^1$ and $R^2$ are the same or different and $R^1$ is a

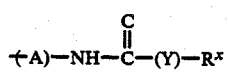

group, in which A and Y are a straight chain or branched alkyl group with 1-6 carbon atoms and $R^x$ is a phenyl radical substituted in the p-position, but not with halogen, or an imidazole radical attached to the 4-position, and if $R^1$ is not the same as $R^2$, then $R^2$ denotes $NO_2$, nitrile or alkoxy with 1-4 carbon atoms, $R^3$ and $R^4$ are the same or different and denote H, $NH_2$ or straight-chain or branched alkyl radicals with 1-4 carbon atoms, $R^5$ denotes an aryl radical which is unsubstituted or is substituted by 1 to 2 identical or different substituents from the group consisting of alkyl, alkoxy, phenyl, halogen, nitro, cyano, trifluoromethyl and alkylmercapto, and in which the radical $R^x$ is also singly or doubly substituted by $^{125}I$ and has a specific activity of about 2200 to about 8800 Ci/mMole.

2. A radioactively labelled 1,4-dihydroxypyridine derivative as defined in claim 1, wherein aryl is a phenyl, naphthyl, thenyl or furyl radical.

3. A radioactively labelled 1,4-dihydropyridine derivative as defined in claim 1, wherein $R^5$ is a phenyl radical which is unsubstituted or singly or doubly substituted by nitro, cyano, trifluoromethyl, trifluoromethoxy, fluorine, chlorine or bromine.

4. A radioactively labelled 1,4-dihydropyridine derivative as defined in claim 1, wherein $R^x$ is

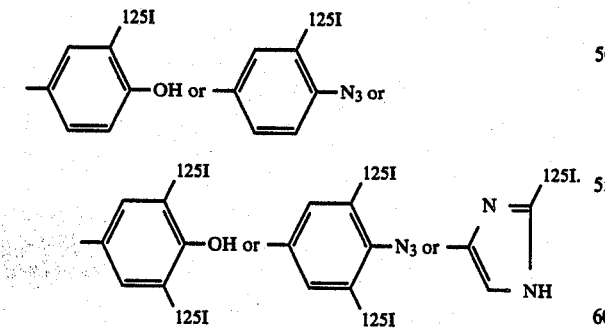

5. A radioactively labelled 1,4-dihydropyridine derivative as defined in claim 4, wherein $R^5$ is a phenyl radical which is unsubstituted or is singly or doubly substituted by nitro, cyano, trifluoromethyl, trifluoromethoxy, fluorine, chlorine or bromine.

6. A radioactively labelled 1,4-dihydroquinoline derivative of the formula

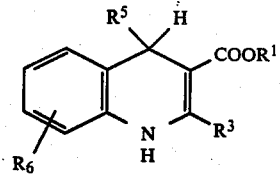

II in which $R^1$ and $R^2$ are the same or different and $R^1$ is a $$\text{+A)}-\text{NH}-\overset{\overset{\text{C}}{\|}}{\text{C}}-(\text{Y})-R^x$$

group, in which A and Y are a straight chain or branched alkyl group with 1-6 carbon atoms and $R^x$ is a phenyl radical substituted in the p-position, but not with halogen, or an imidazole radical attached to the 4-position, $R^3$ is H, $NH_2$ or straight-chain or branched alkyl radicals with 1-4 carbon atoms, $R^5$ denotes an unsubstituted aryl radical or an aryl radical substituted by 1 or 2 identical or different substituents from the group consisting of alkyl, alkoxy, phenyl, halogen, nitro, cyano, trifluoromethyl and alkyl-mercapto, $R^6$ denotes H, halogen, alkyl or alkoxy radical, and in which the radical $R^x$ is also singly or doubly substituted by $^{125}I$ and has a specific activity of about 2200 to about 8800 Ci/mMole.

7. A radioactively labelled 1,4-dihydroquinoline derivative according to claim 6, wherein $R^5$ is a phenyl radical which is unsubstituted or is singly or doubly substituted by nitro, cyano, trifluoromethyl, trifluoromethoxy, fluorine, chlorine or bromine.

8. A radioactively labelled 1,4-dihydroquinoline derivative as defined in claim 2, wherein aryl is a phenyl, naphthyl, thenyl or furyl radical.

9. A radioactively labelled 1,4-dihydroquinoline derivative according to claim 6, wherein $R^x$ is

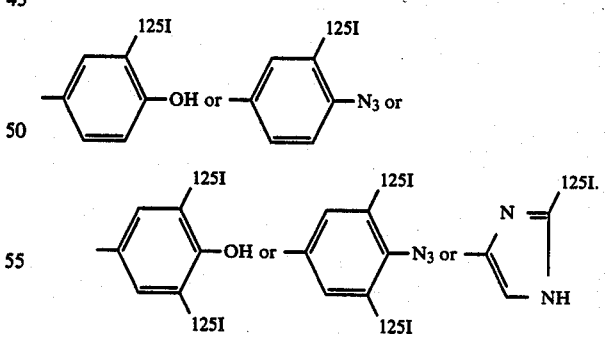

10. A radioactively labelled 1,4-dihydroquinoline derivative as defined in claim 9, wherein $R^5$ is phenyl which is unsubstituted or is singly or doubly substituted by nitro, cyano, trifluoromethyl, trifluoromethoxy, fluorine, chlorine or bromine.

* * * * *